United States Patent [19]

Go et al.

[11] Patent Number: 4,808,618
[45] Date of Patent: Feb. 28, 1989

[54] SUBSTITUTED 1,3-DIALKYLPYRIDO[4,3-D]PYRIMIDINE-2,4-DIONES

[75] Inventors: Kouichiro Go; Yoshiyuki Kurimoto; Norihiko Kitamura, all of Hyogo, Japan

[73] Assignee: Nippon Zoki Pharmaceutical Co., Ltd., Osaka, Japan

[21] Appl. No.: 35,797

[22] Filed: Apr. 8, 1987

[30] Foreign Application Priority Data

Apr. 16, 1986 [JP] Japan .................. 61-89065

[51] Int. Cl.$^4$ .................. A61K 31/505; C07D 471/04
[52] U.S. Cl. .................. 514/258; 544/279; 544/311
[58] Field of Search .................. 514/258; 544/279

[56] References Cited

U.S. PATENT DOCUMENTS 3,186,991 6/1965 Ohnacker .................. 544/279

Primary Examiner—Donald G. Daus
Assistant Examiner—E. Bernhardt
Attorney, Agent, or Firm—Armstrong, Nikaido, Marmelstein & Kubovcik

[57] ABSTRACT

The present invention relates to a novel pyrido[4,3-d]pyrimidine derivative having the formula (I):

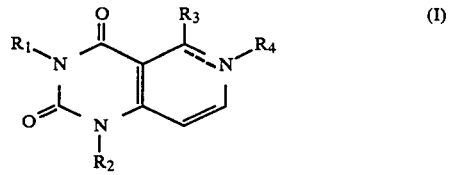

wherein each of $R_1$ and $R_2$, which may be the same or different, is a lower alkyl group; $R_3$ is hydrogen, halogen, hydroxy, amino, hydroxyamino, imino, hydrazino or a lower alkylamino group which may optionally have hydroxy, amino or a lower alkylamino group; and $R_4$ is hydrogen, amino, —NH$^\ominus$ or a lower alkyl group which may optionally have hydroxy, amino or a lower alkylamino group; and pharmaceutically acceptable salt thereof. These compounds are useful as anti-allergic agents, for example, for the treatment of bronchial asthma, urticaria, allergic rhinitis, allergic dermatoses or allergic conjunctivitis.

11 Claims, No Drawings

SUBSTITUTED 1,3-DIALKYLPYRIDO[4,3-D]PYRIMIDINE-2,4-DIONES

BACKGROUND OF THE INVENTION

The present invention relates to novel pyrido[4,3-d]pyrimidine derivatives, pharmaceutically acceptable salts thereof and pharmaceutical compositions containing them as an active ingredient.

It is known that the so-called "chemical mediator", i.e. histamine, serotonin or SRS-A, plays an important role in the appearance of various allergic symptoms in the human body. A pharmaceutical which antagonizes such biochemical substances and/or inhibits their release would be useful for treating or preventing allergic diseases. There have been several prior attempts to synthesize such compounds.

It has been found that certain pyrido[4,3-d]pyrimidine derivatives have an excellent anti-allergic effect.

An object of the present invention is to provide novel pyrido[4,3-d]pyrimidine derivatives and pharmaceutically acceptable salts thereof useful for treating or mitigating the effects of allergic diseases as well as possessing low toxicity and fewer side effects. Another object of the invention is to provide pharmaceutical compositions containing at least one of the pyrido[4,3-d]pyrimidine derivatives or pharmaceutically acceptable salts thereof as an active ingredient. A further object of the present invention is to provide a method for treating mammals suffering from bronchial asthma, urticaria, allergic rhinitis, allergic dermatoses or allergic conjunctivitis which comprises administering thereto the compounds of the invention.

DETEAILED DESCRIPTION OF THE INVENTION

Pyrido[4,3-d]pyrimidine derivatives of the present invention are represented by the following formula (I)

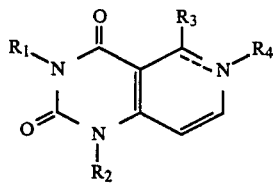

wherein each of $R_1$ and $R_2$, which may be the same or different, is a lower alkyl group; $R_3$ is hydrogen, halogen, hydroxy, amino, hydroxyamino, imino, hydrazino or a lower alkylamino group which may optionally have hydroxy, amino or a lower alkylamino group; and $R_4$ is hydrogen, amino, —NH$^\ominus$ or a lower alkyl group which may optionally have hydroxy, amino or a lower alkylamino group.

Each of $R_1$ and $R_2$, which may be the same or different represents a straight or branched alkyl group having 1 to 5 carbon atoms, such as methyl, ethyl, propyl, isopropyl, butyl, isobutyl, sec-butyl, tert-butyl or pentyl.

$R_3$ represents hydrogen; halogen, such as flouride, chloride, bromide or iodide, preferably chloride; amino; hydroxyamino; imino; hydrazino; or a straight or branched alkylamino group having 1 to 5 carbon atoms, such as methylamino, ethylamino, propylamino, isopropylamino, butylamino, isobutylamino, sec-butylamino, tert-butylamino or pentylamino. The said alkylamino group may optionally have hydroxy, amino or one or two straight or branched alkylamino group having 1 to 3 carbon atoms, such as methylamino, dimethylamino, ethylamino, diethylamino, propylamino or isopropylamino.

$R_4$ represents hydrogen; amino; —NH$^\ominus$; or a straight or branched alkyl group having 1 to 5 carbon atoms, such as methyl, ethyl, propyl, isopropyl, butyl, isobutyl, sec-butyl, tert-butyl or pentyl. The said alkyl group may optionally have hydroxy, amino or one or two straight or branched alkylamino group having 1 to 3 carbon atoms, such as methylamino, dimethylamino, ethylamino, diethylamino, propylamino or isopropylamino.

In the formula (I), the broken line indicates a single bond only when $R_3$ is imino, and in other cases it indicates a double bond.

Preferred compounds of the present invention include:
1,3-dimethylpyrido[4,3-d]pyrimidine-2,4-dione
1,3-dimethylpyrido[4,3-d]pyrimidine-2,4-dione N$^6$-imido
5-amino-1,3-dimethylpyrido[4,3-d]pyrimidine-2,4-dione
5-amino-1,3-diethylpyrido[4,3-d]pyrimidine-2,4-dione
5-amino-1-isobutyl-3-methylpyrido[4,3-d]pyrimidine-2,4-dione
5-methylamino-1,3-dimethylpyrido[4,3-d]pyrimidine-2,4-dione
5-methylamino-1,3-diethylpyrido[4,3-d]pyrimidine-2,4-dione
5-ethylamino-1,3-dimethylpyrido[4,3-d]pyrimidine-2,4-dione
5-isopropylamino-1,3-dimethylpyrido[4,3-d]pyrimidine-2,4-dione
5-hydroxyamino-1,3-dimethylpyrido[4,3-d]pyrimidine-2,4-dione
6-amino-5-imino-1,3-dimethylpyrido[4,3-d]pyrimidine-2,4-dione
6-butyl-5-imino-1,3-dimethylpyrido[4,3-d]pyrimidine-2,4-dione
6-(2-hydroxyethyl)-5-imino-1,3-dimethylpyrido[4,3-d]pyrimidine-2,4dione
5-(2-hydroxyethyl)amino-1,3-dimethylpyrido[4,3-d]pyrimidine-2,4-dione
5-(2-(N,N-dimethylamino)ethylamino)-1,3-dimethylpyrido[4,3-d]pyrimidine-2,4-dione
5-imino-6-(3-(N,N-diethylamino)propyl)-1,3-dimethylpyrido[4,3-d]pyrimidine-2,4-dione
5-hydroxy-1,3-dimethylpyrido[4,3-d]pyrimidine-2,4-dione
5-cloro-1,3-dimethylpyrido[4,3-d]pyrimidine-2,4-dione
5-hydrazino-1,3-dimethylpyrido[4,3-d]pyrimidine-2,4-dione The pyrido[4,3-d]pyrimidine derivatives of the present invention include pharmaceutically acceptable salts of the compounds having formula (I) above, for example, salts with alkali metal such as sodium or potassium, with alkaline-earth metal such as calcium or barium, or with other metals such as aluminum; salts as acid addition with an inorganic acid such as hydrochloric acid, sulfuric acid, nitric acid or phosphoric acid, or with an organic acid such as formic acid, acetic acid, citric acid or lactic acid; or salts with an organic base such as ammonia or the like. These salts can be prepared from pyrido[4,3-d]pyrimidine derivatives or other salts of these derivatives by a known method.

When optical isomers exist in the compounds of the invention, the present invention includes any of the dl, d and l -isomers.

The compounds of the present invention can be prepared as follows.

The compounds having the general formula (II):

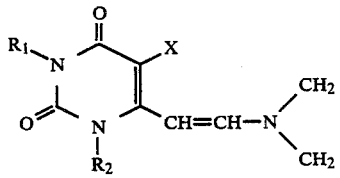

wherein each of $R_1$ and $R_2$, which may be the same or different, is a lower alkyl group and X is cyano or formyl. are reacted with the compounds having the formula (III):

wherein each of Y and Y', which may be the same or different, is hydrogen, hydroxy, amino or a lower alkyl group which may optionally have hydroxy, amino or a lower alkylamino group. in an appropriate solvent such as dimethylformamide (DMF), pyridine or an alcohol such as methanol, ethanol or isopropyl alcohol at room temperature, at a suitable temperature or under reflux for several tens of minutes to several days to give the compounds of the present invention having the formula (I) above.

The compounds of the formula (II) wherein X is cyano are reacted with the compounds of the formula (III) wherein Y and Y' are lower alkyl groups, such as dimethylamine and diethylamine, and then hydroylzed in water to give the compounds of the present invention having hydroxy at 5-position.

The said compounds having hydroxy at 5-position are halogenated by a known method such as a halogenating reaction using oxyphosphorus chloride to give the compound having halogen at 5-position.

The compounds having amino, hydroxyamino, methylamino, ethylamino or hydrazino at 5-position can also be prepared by reacting the said compound having halogen at 5-position with a amine group such as ammonia, hydroxyamine, methylamine, ethylamine, hydrazine or the like.

5-Cyano- or 5-formyl-1,3-dimethyl-6-(2-dimethylamino-vinyl)uracil, the starting materials, can be obtained by reacting 5-cyano- or 5-formyl-1,3,6-trimethyluracil with dimethylformamide dimethylacetal in an appropriate solvent such as absolute DMF for several tens of minutes to several hours under reflux.

The methods of the present invention provided that novel pyrido[4,3-d]pyrimidine-2,4-dione derivatives having various substituents at 5- and/or 7-position can be prepared easily.

The resulting compounds of the present invention can be purified by known methods such as distillation chromatography and recrystallization. Identification is established through, inter alia, elemental analysis, melting point, IR, NMR, UV, mass spectrum, etc.

EXAMPLES

The following examples, which are illustrative only and not intended to limit the scope of the invention, described the preparation of the compounds of the present invention.

EXAMPLE 1

(1) 0.47 g of 5-formyl-1,3-dimethyl-6-(2-dimethylaminovinyl)uracil was dissolved in ethanol, and ammonia was added thereto. The solution was stirred for 30 min at room temperature. The precipitated crystals were separated from the solution by filtration and recrystallized from ethanol to give 0.32 g of 1,3-dimethylpyrido[4,3-d]pyrimidine-2,4-dione (Compound 1).

Yield: 83.8%.
m.p.: 174°–175° C.
Elementary Analysis: $C_9H_9N_3O_2$:

|  | C % | H % | N % |
| --- | --- | --- | --- |
| Calculated | 56.54 | 4.75 | 21.98 |
| Found | 56.53 | 4.78 | 22.00 |

NMR(DMSO-$d_6$): $\delta$=3.24(3H, s), 3.42(3H, s), 8.96(1H, d, J=1 Hz), 7.40(1H, d, J=6 Hz), 8.68(1H, dd, J=1 Hz, 6 Hz).

(2) In the same manner, using hydrazine hydrate instead of ammonia, 1,3-dimethylpyrido[4,3-d]pyrimidine-2,4-dione $N^6$-imido (Compound 2) having the following formula.

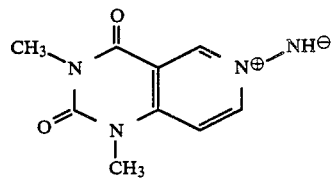

Yield: 78.1%.
m.p.: 219°–220° C. (decomposition).
Elementary Analysis: $C_9H_{10}N_4O_2 \cdot 3/20 H_2O$:

|  | C % | H % | N % |
| --- | --- | --- | --- |
| Calculated | 51.74 | 4.47 | 26.82 |
| Found | 51.95 | 4.90 | 26.57 |

NMR($CF_3COOH$): $\delta$=3.60(3H, s), 3.80(3H, s), 7.80(1H, d, J=7 Hz), 8.83(1H, dd, J=1 Hz, 7 Hz), 9.51(1H, d, J=1 Hz).

EXAMPLE 2

(1) 1.0 g of 5-cyano-1,3-dimethyl-6-(2-dimethylaminovinyl)uracil and 5.0 ml of 30% ammonia aqueous solution were added to 22.5 ml of DMF. The solution was heated at 100° C. in a sealed tube for 24 hr. The precipitated crystals were separated by filtration, washed with ether and recrystallized from ethanol to give 0.61 g of 5-amino-1,3-dimethylpyrido[4,3-d]pyrimidine-2,4-dione (Compound 3).

Yield: 70.0%.
m.p.: 229°–230° C.
Elementary Analysis: $C_9H_{10}N_4O_2$:

| | C % | H % | N % |
|---|---|---|---|
| Calculated | 52.42 | 4.89 | 27.12 |
| Found | 52.60 | 4.92 | 27.02 |

NMR(DMSO-$d_6$): δ=3.27(3H, s), 3.40(3H, s), 6.45(1H, d, J=7 Hz), 6.45(1H, d, J=7 Hz), 8.08(1H, d, J=6 Hz).

In the same manner, the following compounds were obtained.

5-amino-1,3-diethylpyrido[4,3-d]pyrimidine-2,4-dione (Compound 4)
Yield: 62.7%.
m.p.: 181°–183° C.
Elementary Analysis: $C_{11}H_{14}N_4O_2$:

| | C % | H % | N % |
|---|---|---|---|
| Calculated | 56.40 | 6.02 | 23.92 |
| Found | 56.52 | 6.02 | 23.96 |

NMR(CDCl$_3$): δ=1.28(3H, t, J=7 Hz), 1.31(3H, t, J=7 Hz), 4.12(4H, q, J=7 Hz), 6.35(1H, d, J=6 Hz), 8.16(1H, d, J=6 Hz).

5-amino-1-isobutyl-3-methylpyrido[4,3-d]pyrimidine-2,4-dione (Compound 5)
Yield: 73.3%.
m.p.: 167° C.
Elementary Analysis: $C_{12}H_{16}N_4O_2$:

| | C % | H % | N % |
|---|---|---|---|
| Calculated | 58.05 | 6.50 | 22.57 |
| Found | 58.23 | 6.51 | 22.58 |

NMR(CDCl$_3$): δ=0.95(6H, d, J=6 Hz), 2.20(1H, br), 3.40(3H, s), 3.90(2H, d, J=7 Hz), 6.31(1H, d, J=6 Hz), 8.15(1H, d, J=6 Hz).

(2) In the same manner, using methylamine or isopropylamine instead of ammonia, the following compounds were obtained.

5-methylamino-1,3-dimethylpyrido[4,3-d]pyrimidine-2,4-dione (Compound 6)
Yield: 67.0%.
m.p.: 228°–229° C.
Elementary Analysis: $C_{10}H_{12}N_4O_2$:

| | C % | H % | N % |
|---|---|---|---|
| Calculated | 54.54 | 5.49 | 25.44 |
| Found | 54.79 | 5.57 | 25.41 |

5-methylamino-1,3-diethylpyrido[4,3-d]pyrimidine-2,4-dione (Compound 7)
Yield: 44.9%.
m.p.: 103°–105° C.
Elementary Analysis: $C_{12}H_{16}N_4O_2$:

| | C % | H % | N % |
|---|---|---|---|
| Calculated | 58.05 | 6.50 | 22.57 |
| Found | 58.14 | 6.56 | 22.70 |

NMR(CDCl$_3$): δ=1.25(3H, t, J=7 Hz), 1.33(3H, t, J=7 Hz), 3.09(3H, d, J=5 Hz), 4.11(4H, q, J=7 Hz), 6.28(1H, d, J=6 Hz), 8.25(1H, d, J=6 Hz), 9.05(1H, br).

5-isopropylamino-1,3-dimethylpyrido[4,3-d]pyrimidine-2,4-dione (Compound 8)
Yield: 50%.
m.p.: 117° C.
Elementary Analysis: $C_{12}H_{16}N_4O_2$:

| | C % | H % | N % |
|---|---|---|---|
| Calculated | 58.05 | 6.50 | 22.57 |
| Found | 58.26 | 6.68 | 22.76 |

NMR(DMSO-$d_6$): δ=1.22(6H, d, J=6.5 Hz), 3.25(3H, s), 3.40(3H, s), 4.29(1H, m), 6.45(1H, d, J=6 Hz), 8.15(1H, d, J=6.0 Hz), 8.82(1H, d, J=7.5 Hz).

(3) In the same manner, using hydroxyamine instead of ammonia, 5-hydroxyamino-1,3-dimethylpyrido[4,3-d]pyrimidine-2,4-dione (Compound 9) was obtained.
Yield: 88.6%.
m.p.: >300° C.
Elementary Analysis: $C_9H_{10}N_4O_3$:

| | C % | H % | N % |
|---|---|---|---|
| Calculated | 48.65 | 4.54 | 25.22 |
| Found | 48.61 | 4.51 | 25.13 |

NMR(CF$_3$COOH): δ=3.38(3H, s), 3.62(3H, s), 7.57(1H, d, J=7.1 Hz), 8.64(1H, d, J=7.1 Hz), 9.25(1H, br), 9.55(1H, br).

(4) In the same manner, using hydrazine hydrate instead of ammonia, 6-amino-5-imino-1,3-dimethylpyrido[4,3-d]pyrimidine-2,4-dione (Compound 10) was obtained.
Yield: 86.8%.
m.p.: 258°–259° C. (decomposition).
Elementary Analysis: $C_9H_{11}N_5O_2$:

| | C % | H % | N % |
|---|---|---|---|
| Calculated | 48.86 | 5.01 | 31.66 |
| Found | 48.69 | 5.05 | 31.57 |

NMR(CF$_3$COOH): δ=3.53(3H, s), 3.70(3H, s), 6.88(1H, d, J=7 Hz), 8.13(1H, br), 8.26(1H, d, J=7 Hz).

(5) In the same manner, using n-butylamine instead of ammonia, 6-butylamino-5-imino-1,3-dimethylpyrido[4,3-d]pyrimidine-2,4-dione (Compound 11) was obtained.
Yield: 93.4%.
m.p.: 199° C.
Elementary Analysis: $C_{13}H_{18}N_4O_2$:

| | C % | H % | N % |
|---|---|---|---|
| Calculated | 59.52 | 6.92 | 21.36 |
| Found | 59.54 | 6.92 | 21.29 |

NMR(CDCl$_3$): δ=0.80;14 2.00(7H, br), 3.41(3H, s), 3.50(3H, s), 3.97(2H, t, J=7 Hz), 5.64(1H, d, J=7 Hz), 7.32(1H, d, J=7 Hz), 9.58(1H, br).

(6) In the same manner, using 2-aminoethanol instead of ammonia, the following compounds were obtained.
6-(2-hydroxyethyl)-5-imino-1,3-dimethylpyrido[4,3-d]pyrimidine-2,4-dione (Compound 12)
Reaction: refluxing for 10 hr in methanol.
Yield: 56%.
m.p.: 210° C. (decomposition).
Elementary Analysis: $C_{11}H_{14}N_4O_3$:

|            | C %   | H %  | N %   |
|------------|-------|------|-------|
| Calculated | 52.79 | 5.64 | 22.39 |
| Found      | 52.91 | 5.85 | 22.26 |

NMR(DMSO-$d_6$): δ=3.22(3H, s), 3.39(3H, s), 3.64(2H, t, J=5 Hz), 3.99(2H, t, J=5 Hz), 5.16(1H, bs), 5.90(1H, t, J=7.5 Hz), 7.66(1H, d, J=7.5 Hz), 9.12(1H, s).

5-(2-hydroxyethyl)amino-1,3-dimethylpyrido[4,3-d]pyrimidine-2,4-dione (Compound 13)
Reaction: heating for 20 hr at 100° C. in DMF.
Yield: 56%.
m.p.: >200° C.
IR(KBr): 3350, 1710, 1680, 1660, 1530, 1050 cm$^{-1}$.
NMR(DMSO-$d_6$): δ=3.19(3H, s), 3.43(3H, s), 3.61(2H, t, J=5 Hz), 3.94(2H, t, J=5 Hz), 4.87(1H, br), 6.36(1H, d, J=7.5 Hz), 7.90(1H, d, J=7.5 Hz).

(7) In the same manner, using 2-dimethylaminoethylamine instead of ammonia, 5-(2-(N,N-dimethylamino)ethylamino)-1,3-dimethylpyrido[4,3-d]pyrimidine-2,4-dione (Compound 14) was obtained.
Reaction: heating at 100° C. for 20 hr in DMF.
Yield: 36%.
m.p.: 179°–180° C.
Elementary Analysis: $C_{13}H_{19}N_5O_2$:

|            | C %   | H %  | N %   |
|------------|-------|------|-------|
| Calculated | 56.30 | 6.91 | 25.25 |
| Found      | 56.13 | 7.14 | 25.02 |

NMR(DMSO-$d_6$): δ=2.17(6H, s), 2.46(2H, t, J=6 Hz), 3.25(3H, s), 3.39(3H, s), 3.52(2H, ddd, J=5 Hz, 6 Hz), 6.44(1H, d, J=6 Hz), 8.14(1H, d, J=6 Hz), 9.01(1H, t, J=5 Hz).

(8) In the same manner, using 3-diethylaminopropylamine instead of ammonia, 5-imino-6-(3-(N,N-diethylamino)propyl)-1,3-dimethylpyrido[4,3-d]pyrimidine-2,4-dione (Compound 15) was obtained.
Reaction: refluxing for 10 hr in methanol.
Yield: 43.8%.
m.p.: 68° C.
IR(KBr): 3300, 1700, 1640, 1580, 1560 cm$^{-1}$.
NMR(DMSO-$d_6$): δ=0.94(6H, s), 2.46(2H, t, J=6 Hz), 3.25(3H, s), 3.39(3H, s), 3.52(2H, ddd, J=5 Hz, 6 Hz), 6.44(1H, d, J=6 Hz), 8.14(1H, d, J=6 Hz), 9.01(1H, t, J=5 Hz).

EXAMPLE 3

(1) 1.85 g of 5-cyano-1,3-dimethyl-6-(2-dimethylaminovinyl)uracil and 1.32 g of dimethylamine hydrochloride were added to 40 ml of pyridine, and the solution was heated under reflux for 12 hr. 1.32 g of dimethylamine hydrochloride was added and the solution was heated under reflux for 36 hr. After the solvent was distilled off, water added to the residue. The precipitated crystals were separated by filtration and recrystallized from water to give 1.12 g of 5-hydroxy-1,3-dimethylpyrido[4,3-d]pyrimidine-2,4-dione (Compound 16).
Yield: 68%.
m.p.: >300° C.
Elementary Analysis: $C_9H_9N_3O_3 \cdot \frac{1}{2}H_2O$:

|            | C %   | H %  | N %   |
|------------|-------|------|-------|
| Calculated | 50.00 | 4.66 | 19.44 |
| Found      | 49.91 | 4.67 | 19.38 |

NMR(DMSO-$d_6$): δ=3.23(3H, s), 3.48(3H, s), 6.41(1H, d, J=8 Hz), 7.78(1H, d, J=8 Hz), 11.78(1H, brs).

(2) 0.72 g of Compound 16 was added to 20 ml of oxyphosphorus chloride and the solution was heated for 8 hr at 80° C. After the solvent was distilled off, the crude crystals precipitated by adding water to the residue was separated by filtration, washed with water and recrystallized from benzene to give 0.65 g of 5-chloro-1,3-dimethylpyrido[4,3-d]pyrimidine-2,4-dione (Compound 17).
Yield: 83%.
m.p.: 220° C.
Elementary Analysis: $C_9H_8ClN_3O_2$.

|            | C %   | H %  | N %   |
|------------|-------|------|-------|
| Calculated | 47.91 | 3.57 | 18.62 |
| Found      | 47.91 | 3.47 | 18.45 |

NMR(DMSO-$d_6$): δ=3.29(3H, s), 3.50(3H, s), 7.47(1H, d, J=6 Hz), 8.48(1H, d, J=6 Hz).

(3) 0.69 g of Compound 17 and 0.31 g of hydrazine hydrate were added to 20 ml of methanol and the solution was heated under reflux for 24 hr. The solvent was distilled off to give 0.63 g of 5-hydrazino-1,3-dimethylpyrido[4,3-d]pyrimidine-2,4-dione (Compound 18).
Yield: 93%.
m.p.: 244° C.
Elementary Analysis: $C_9H_{11}N_5O_2$:

|            | C %   | H %  | N %   |
|------------|-------|------|-------|
| Calculated | 48.86 | 5.01 | 31.66 |
| Found      | 49.08 | 5.05 | 31.69 |

NMR(DMSO-$d_6$): δ=3.32(3H, s), 3.56(3H, s), 7.02(1H, d, J=7 Hz), 8.32(1H, d, J=7 Hz), 10.44(1H, br).

Pharmaceutical studies on the compounds of the present invention are now described below.

(1) Acute toxicity test

The test compounds were orally administered to groups of 5 ICR-strainmale mice. $LD_{50}$ value of the compound of the present invention was calculated by the Litchfield-Wilcoxon's method based on mortality for 14 days after drug administration. An example of the results is shown in Table 1.

TABLE 1

| Test compound | $LD_{50}$ (mg/kg) |
|---------------|-------------------|
| Compound 1    | 400               |
| Compound 3    | 710               |
| Compound 6    | 720               |
| Compound 8    | 700               |

(2) Anti-allergic effect

PCA (Passive Cutaneous Anaphylaxis) reaction in rats was taken as an index to an anti-allergic effect of the compound of the present invention.

In order to perform sensitization, anti-DNP-Asc (dinitrophenylated Ascaris extracts) serum diluted with saline was injected intradermally at 4 sites on the shaved back of groups of 6 Wister-strain male rats (6 weeks of age). 1 hour after oral administration of the test drug, the mixture of equivalent amount of DNP-Asc (5 mg/ml) and 2% Evans blue were intravenously injected to generate PCA reaction. 30 minutes thereafter, rats were killed by decapitation and exsanguinated. The skin was opened in order to evaluate the leakage of blue dye. The obtained skin was dissolved in 2N potassium hydroxide, then 2N phosphoric acid and acetone were added thereto. The amount of dye was determined by measurement of absorbance at 620 nm after centrifugation.

An example of the results is shown in Table 2.

TABLE 2

| Test compound | Dosage (mg/kg) | Inhibition (%) |
|---|---|---|
| control | — | 0 |
| Compound 1 | 20 | 85.3 |
| Compound 3 | 20 | 77.3 |
| Compound 4 | 20 | 89.3 |
| Compound 6 | 20 | 92.0 |
| Compound 7 | 20 | 72.7 |
| Compound 8 | 20 | 73.4 |
| Theophylline | 20 | 78.7 |

As is clearly apparent from the above mentioned results, the pyrido[4,3-d]pyrimidine derivatives of the present invention have excellent anti-allergic properties which are superior to those of conventional pharmaceuticals, for example, theophylline. Furthermore, the compounds of the invention possess low toxicity, so that they have good safety properties. They are useful in the prevention or treatment of various allergic diseases, such as bronchial asthma, urticaria, allergic rhinitis, allergic dermatoses or allergic conjunctivitis. In addition, since the compounds of the present invention can be administered orally, they can be used in the treatment of chronic diseases.

As another index of anti-allergic effect of the compound of the present invention different from the PCA reaction, the phosphodiesterase (PDE) inhibiting effect was tested. As the results, the compounds of the present invention effectively inhibited PDE activity even at very low concentrations. The compounds of the present invention have excellent PDE inhibiting effect, so that they are not only useful as anti-allergic agents, but also as cardiotonics, bronchdilator and the like.

The compounds of the present invention can be made into pharmaceutical compositions by combination with appropriate medicinal carriers or diluents, and can be formulated into preparations in solid, semisolid, liquid or gaseous form such as tablets, capsules, powders, granules, ointments, solutions, suppositories, injections, inhalants, aerosols and cataplasms in usual ways for oral or parenteral administrations.

In pharmaceutical dosage forms, the compounds of the present invention can be used in the form of their pharmaceutically acceptable salts, and also can be used alone or in appropriate association, as well as in combination with other pharmaceutically active components such as a bronchodilator, antihistaminic or tranquilizer.

In case of oral preparations, the compounds can be used alone or combined with appropriate additives to make tablets, powders, granules or capsules, e.g. with conventional additives such as lactose, mannitol, corn starch or potato starch; with binders such as crystalline cellulose, cellulose derivatives, acacia, corn starch or gelatins; with disintegrators such as corn starch, potato starch or sodium carboxymethylcellulose; with lubricants such as talc or magnesium stearate; and if desired, with diluents, buffering agents, moistening agents, preservatives and flavoring agents.

The compounds of the invention can also be made into an ointment by combination with an ointment base such as vaseline, paraffin, plastibase, simple ointment, hydrophilic ointment, hydrophilic vaseline or hydrophilic plastibase.

Furthermore, the compounds of the invention can be made into a suppository by mixing with a variety of bases, e.g. fatty and oily base such as cacao butter, emulsifying base or water-soluble base such as macrogol.

The compounds of the present invention can be formulated into a preparations for injections by dissolving, suspending or emulsifying in aqueous or non-aqueous solvent, such as distilled water for injection, physiologically saline solution, vegetable oil, synthetic aliphatic acid glycerides, esters of higher aliphatic acid or propylene glycol.

In case of inhalations or aerosol preparations, the compounds of the invention in the form of a liquid or minute powder can be filled up in an aerosol container with gas or liquid spraying agent, and if desired, with conventional adjuvants such as humidifying agents or dispersing agent. They can also be used as pharmaceuticals for a non-pressurized preparation such as in a nebulizer or an atomizer.

In order to make the compounds of the present invention into collyriums, they can be prepared as a solution or suspension together with an aqueous solvent such as sterile, purified water and physiologically saline solution, or a non-aqueous solvent for injection.

Cataplasms can be prepared by mixing the compounds with mentha oil, concentrated glycerin, kaolin or other suitable additives.

The desirable dose of the compounds of the present invention varies with the subject, form of the drug, method and period of administration. However, in order to obtain desirable effects, generally it is recommended to administer orally 1 to 1000 mg/kg, preferably 5 to 600 mg/kg daily. Unit preparations are also recommended for administration in one to several units daily.

In case of parenteral administrations e.g. injections, doses of the compounds in the order of one tenth to one third of the above dose are preferable as daily doses.

Some prescriptions of the pharmaceutical compositions are shown below as examples which contain the compounds of the present invention as active ingredients.

| Prescription example 1 (tablet) | |
|---|---|
| Component | Content in a tablet (mg) |
| compound of this invention | 100 |
| lactose | 130 |
| corn starch | 40 |
| magnesium stearate | 10 |
| Total | 280 mg |

| Prescription example 2 (capsule) | |
|---|---|
| Component | Content in a capsule (mg) |
| compound of this invention | 50 |
| lactose | 250 |
| Total | 300 mg |

-continued

Prescription example 3 (injection)

| Component | Content in an ampule (mg) |
| --- | --- |
| compound of this invention | 10 |
| sodium chloride | proper amount |
| distilled water for injection | proper amount |
| Total | 1 ml |

Prescription example 4 (ointment)

| Component | Weight (g) |
| --- | --- |
| compound of this invention | 1 |
| emulsified wax | 30 |
| white petrolatum | 50 |
| liquid paraffin | 20 |
| Total | 101 g |

Prescription example 5 (suppository)

| Component | Content in a suppository (mg) |
| --- | --- |
| compound of this invention | 20 |
| cacao butter | 1980 |
| Total | 2000 mg |

Prescription example 6 (inhalation)

| Component | Content in a inhalation (g) |
| --- | --- |
| compound of this invention | 1 |
| lactose | 5 |
| Total | 6 g |

What we claim is:

1. A pyrido[4,3-d]pyrimidine compound of the formula

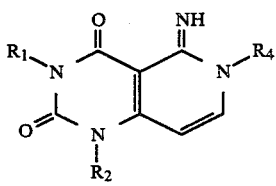

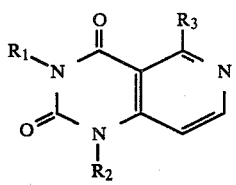

or

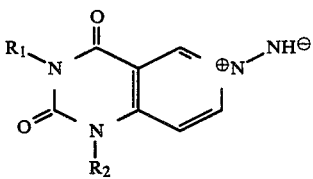

wherein each $R_1$ and $R_2$, which may be the same or different, is a lower alkyl group; $R_3$ is halogen, hydroxy, amino, hydroxyamino, hydrazino or a lower alkylamino group which may optionally have hydroxy, amino or a lower alkylamino group and $R_4$ is hydrogen, amino, or a lower alkyl group which may optionally have hydroxy, amino or a lower alkylamino group; or pharmaceutically acceptable salt thereof.

2. A pyrido[4,3-d]pyrimidine compound of the formula

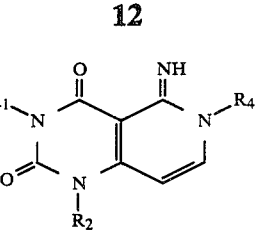

wherein each $R_1$ and $R_2$, which may be the same or different, is a lower alkyl group; and $R_4$ is hydrogen, amino, or a lower alkyl group which may optionally have hydroxy, amino or a lower alkylamino group; or pharmaceutically acceptable salt thereof.

3. A pyrido[4,3-d]pyrimidine compound of the formula

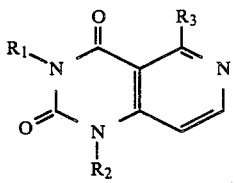

wherein each of $R_1$ and $R_2$, which may be the same or different, is a lower alkyl group; and $R_3$ is halogen, hydroxy, amino, hydroxyamino, hydrazino or a lower alkylamino group which may optionally have hydroxy, amino or a lower alkylamino group; or pharmaceutically acceptable salt thereof.

4. A pyrido[4,3-d]pyrimidine compound of the formula

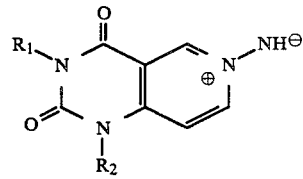

wherein each of $R_1$ and $R_2$, which may be the same or different, is a lower alkyl group; or pharmaceutically acceptable salt thereof.

5. A pyrido[4,3-d]pyrimidine compound according to claim 2 wherein $R_4$ is hydrogen or pharmaceutically acceptable salt thereof.

6. A pyrido[4,3-d]pyrimidine compound according to claim 3 wherein $R_3$ is amino or pharmaceutically acceptable salt thereof.

7. A pyrido[4,3-d]pyrimidine compound according to claim 6 which is 5-amino-1,3-dimethylpyrido[4,3-d]pyrimidine-2,4-dione, 5-amino-1,3-diethylpyrido[4,3-d]pyrimidine-2,4-dione, 5-amino-1-isobutyl-3-methylpyrido[4,3-d]pyrimidine-2,4-dione, or pharmaceutically acceptable salt thereof.

8. A pyrido[4,3-d]pyrimidine compound according to claim 3 wherein $R_3$ is a lower alkylamino group or pharmaceutically acceptable salt thereof.

9. A pyrido[4,3-d]pyrimidine compound according to claim 8 which is 5-methylamino-1,3-dimethylpyrido[4,3-d]pyrimidine-2,4-dione, 5-methylamino-1,3-diethylpyrido[4,3-d]pyrimidine-2,4-dione, 5-isopropylamino-1,3-dimethylpyrido[4,3-d]pyrimidine-2,4-dione, or pharmaceutically acceptable salt thereof.

10. An anti-allergic composition comprising an anti-allergic effective amount of a compound according to claim 1 together with a pharmaceutically acceptable carrier.

11. A method for preventing or treating allergic disease in a mammal which comprises administering thereto an anti-allergic effective amount of a compound according to claim 1.

* * * * *